(12) United States Patent
Xiong et al.

(10) Patent No.: US 12,282,008 B2
(45) Date of Patent: Apr. 22, 2025

(54) METHODS OF REDUCING THE OCCURANCE OF FALSE POSITIVES IN GAS DETECTORS

(71) Applicant: Carrier Corporation, Palm, FL (US)

(72) Inventors: Ziyou Xiong, Wethersfield, CT (US); Michael Birnkrant, Whethersfield, CT (US); Marcin Piech, East Hampton, CT (US)

(73) Assignee: CARRIER CORPORATION, Palm Beach Gardens, FL (US)

( * ) Notice: Subject to any disclaimer, the term of this patent is extended or adjusted under 35 U.S.C. 154(b) by 281 days.

(21) Appl. No.: 17/805,174

(22) Filed: Jun. 2, 2022

(65) Prior Publication Data

US 2023/0020905 A1 Jan. 19, 2023

Related U.S. Application Data

(60) Provisional application No. 63/203,246, filed on Jul. 14, 2021.

(51) Int. Cl.
*G01N 33/00* (2006.01)

(52) U.S. Cl.
CPC ..... *G01N 33/0067* (2013.01); *G01N 33/0063* (2013.01)

(58) Field of Classification Search
CPC ........... G01N 33/0067; G01N 33/0063; G01N 33/0009; G01N 33/0065; F24F 11/36; G01M 3/04; F25B 49/00; F25B 2500/222; G01D 21/02

See application file for complete search history.

(56) References Cited

U.S. PATENT DOCUMENTS

| | | | |
|---|---|---|---|
| 4,337,516 A | 6/1982 | Murphy et al. |
| 4,535,598 A | 8/1985 | Mount |
| 4,660,386 A | 4/1987 | Hansen et al. |
| 5,079,930 A | 1/1992 | Beaverson et al. |

(Continued)

FOREIGN PATENT DOCUMENTS

| | | |
|---|---|---|
| CN | 104360419 B | 2/2017 |
| EP | 3505842 A1 | 7/2019 |

(Continued)

OTHER PUBLICATIONS

Extended European Search Report received for EP Application No. 22179420.9, mailed on Nov. 14, 2022, 8 Pages.

*Primary Examiner* — Xin Y Zhong
(74) *Attorney, Agent, or Firm* — Souad Hakim

(57) ABSTRACT

A method of indicating the presence of a target gas in a gas volume comprising providing a gas sensing core, configured for detection of the target gas, and a condition sensor within the gas volume, providing a controller, allowing gas to fluidly interact with the gas sensing core, monitoring a target gas measurement output from the gas sensing core, monitoring a parameter output from the condition sensor, recording a parameter output minimum value, calculating a parameter difference, calculating a rate of change of the parameter with respect to time, and indicating the presence of a target gas is detected in the gas volume when the target gas measurement exceeds a target gas measurement threshold value and the parameter difference is less than a parameter difference threshold value.

15 Claims, 7 Drawing Sheets

(56) References Cited

U.S. PATENT DOCUMENTS

| | | | |
|---|---|---|---|
| 6,091,324 | A | 7/2000 | Arsenault et al. |
| 6,205,798 | B1 | 3/2001 | Porter et al. |
| 10,539,358 | B2 | 1/2020 | Suzuki et al. |
| 10,859,299 | B2 | 12/2020 | Tanaka et al. |
| 2005/0126190 | A1 | 6/2005 | Lifson et al. |
| 2008/0175759 | A1 | 7/2008 | Oishi |
| 2017/0370605 | A1* | 12/2017 | Makino .................. F24F 11/36 |
| 2020/0264147 | A1 | 8/2020 | Joshi et al. |
| 2021/0048364 | A1* | 2/2021 | Yin ....................... E03B 7/071 |

FOREIGN PATENT DOCUMENTS

| | | |
|---|---|---|
| EP | 3591304 A1 | 1/2020 |
| EP | 3643980 A1 | 4/2020 |
| JP | 2009024923 A | 2/2009 |
| JP | 2017053514 A | 3/2017 |
| JP | 2017207245 A | 11/2017 |
| JP | 6585967 B2 | 10/2019 |
| WO | 2004016999 A1 | 2/2004 |
| WO | 2020021593 A1 | 1/2020 |

\* cited by examiner

METHODS OF REDUCING THE OCCURANCE OF FALSE POSITIVES IN GAS DETECTORS

CROSS REFERENCE TO A RELATED APPLICATION

The application claims the benefit of U.S. Provisional Application No. 63/203,246 filed Jul. 14, 2021, the contents of which are hereby incorporated in their entirety.

BACKGROUND

Exemplary embodiments pertain to the art of gas detection. More particularly, the present disclosure relates to methods and configurations of gas detection systems.

As worldwide environmental regulations or global warming gases evolve, new restrictions aim to reduce the amount of charge contained in refrigerant systems and to force substitution of mildly flammable and flammable refrigerants over traditional refrigerants for their greener properties (e.g., lower global warming potential (GWP)). With the entry of mildly flammable and flammable refrigerants into the consumer air conditioning and refrigeration markets there can be concern over the safety of these devices. Consequently, regulations aim to mandate safety measures to ensure product safety, such as inclusion of sensors capable to warning users in the event or a refrigerant leakage. Accordingly, there remains a need in the art to develop robust, low cost methods of leak detection for these systems to ensure product safety.

BRIEF DESCRIPTION

Disclosed is a method of indicating the presence of a target gas in a gas volume comprising: providing a gas sensing core, configured for detection of the target gas, and a condition sensor within the gas volume, providing a controller disposed in electrical communication with the gas sensing core and the condition sensor, allowing gas within the gas volume to fluidly interact with the gas sensing core, monitoring with the controller a target gas measurement output from the gas sensing core, monitoring with the controller a parameter output from the condition sensor, recording a parameter output minimum value in a memory of the controller, calculating with the controller a parameter difference, wherein the parameter difference is the difference between the minimum value of the parameter and an instant value of the parameter, calculating with the controller a rate of change of the parameter with respect to time, and indicating the presence of a target gas is detected in the gas volume when the target gas measurement exceeds a target gas measurement threshold value and the parameter difference is less than a parameter difference threshold value.

In addition to one or more of the above disclosed aspects or as an alternate, further comprising indicating the presence of a target gas is detected in the gas volume when the target gas measurement exceeds the target gas measurement threshold value, the parameter difference exceeds the parameter difference threshold value, and the rate of change of the parameter with respect to time is less than a rate threshold value.

In addition to one or more of the above disclosed aspects or as an alternate, further comprising not indicating the presence of the target gas is detected in the gas volume when target gas measurement exceeds a target gas threshold value, the parameter difference exceeds the parameter difference threshold value, and the rate of change of the parameter with respect to time exceeds a rate threshold value.

In addition to one or more of the above disclosed aspects or as an alternate, further comprising locating the gas sensing core and the condition sensor in an HVAC/R device, wherein the gas volume is adjacent a flammable refrigerant containing component of the HVAC/R device.

In addition to one or more of the above disclosed aspects or as an alternate, further comprising locating the gas sensing core and the condition sensor at or below a substantial portion of a heat exchanger of an HVAC/R device.

In addition to one or more of the above disclosed aspects or as an alternate, wherein indicating a presence of the target gas comprises signaling to a system controller of a HVAC/R device that target gas is detected, activating an indicator light in electrical communication with the controller, annunciating an alarm through a speaker in electrical communication with the controller, or a combination comprising at least one of the foregoing.

In addition to one or more of the above disclosed aspects or as an alternate, wherein the recording the parameter output minimum value further comprises recording the parameter output minimum value from the condition sensor over a timespan of 3 minutes.

In addition to one or more of the above disclosed aspects or as an alternate, wherein the calculating with the controller a rate of change of the parameter output with respect to time further comprises calculating the rate of change from the parameter output minimum value and a corresponding timestamp, to the instant parameter output and corresponding instant timestamp.

In addition to one or more of the above disclosed aspects or as an alternate, wherein the condition sensor comprises a temperature sensor, or a humidity sensor.

In addition to one or more of the above disclosed aspects or as an alternate, wherein the gas sensing core comprises a combustible gas sensor, a flammable gas sensor, a radon sensor, a smoke sensor, a carbon monoxide sensor, a hydrogen sulfide sensor, a particulate matter sensor, a volatile organic compound sensor, an oxygen sensor, a formaldehyde sensor, a lead sensor, a pesticide sensor, a nitrogen dioxide sensor, or a carbon dioxide sensor.

In addition to one or more of the above disclosed aspects or as an alternate, wherein the target gas measurement threshold value is greater than or equal to 5% and less than or equal to 25% of the lower flammability limit of a flammable refrigerant contained within a flammable refrigerant containing component of a HVAC/R device.

In addition to one or more of the above disclosed aspects or as an alternate, wherein the gas sensing core comprises a combustibility sensor, and wherein the target gas measurement threshold value is equal to 16.6% of the lower flammability limit of R-454B.

In addition to one or more of the above disclosed aspects or as an alternate, wherein the gas sensing core comprises a R-454B gas sensor, and wherein the target gas measurement threshold value is equal to 11.6 volume % R-454B.

In addition to one or more of the above disclosed aspects or as an alternate, wherein the condition sensor comprises a temperature sensor, and wherein the parameter difference threshold value is greater than 2° C.

In addition to one or more of the above disclosed aspects or as an alternate, wherein the condition sensor comprises a temperature sensor, and wherein the parameter difference threshold value is 2.35° C.

In addition to one or more of the above disclosed aspects or as an alternate, wherein the condition sensor comprises a humidity sensor, and wherein the parameter difference threshold value is greater than 5% relative humidity.

In addition to one or more of the above disclosed aspects or as an alternate, wherein the condition sensor comprises a humidity sensor, and wherein the parameter difference threshold value is 10% relative humidity.

In addition to one or more of the above disclosed aspects or as an alternate, wherein the condition sensor comprises a temperature sensor, and wherein the rate threshold value is greater than 1.5° C./minute.

In addition to one or more of the above disclosed aspects or as an alternate, wherein the condition sensor comprises a temperature sensor, and wherein the rate threshold value is 1.76° C./minute.

Further disclosed is an HVAC/R system comprising: a vapor compression device containing flammable refrigerant and a system controller, a gas sensing module disposed in fluid communication with a gas volume surrounding at least a portion of the vapor compression device, wherein the gas sensing module comprises a gas sensing core configured to measure a target gas measurement output and a condition sensor configured to measure a parameter output, a controller disposed in electrical communication with the system controller, the gas sensing core and the condition sensor, wherein the controller is configured to initiate a control action in response to a determination that a target gas is detected by the gas sensing module.

In addition to one or more of the above disclosed aspects or as an alternate, wherein the determination of the gas sensing core is disregarded as erroneous when: the target gas measurement exceeds a target gas measurement threshold value, a parameter difference exceeds a parameter difference threshold value, wherein the parameter difference comprises a difference between the parameter output and a minimum parameter output value stored in a memory of the controller, and a rate of change of the parameter with respect to time exceeds a rate threshold value, wherein the rate of change of the parameter with respect to time comprises the parameter difference divided by a timespan between the instant time and a timestamp of the minimum parameter output value was stored in the memory of the controller.

BRIEF DESCRIPTION OF THE DRAWINGS

The following descriptions should not be considered limiting in any way. With reference to the accompanying drawings, like elements are numbered alike.

DETAILED DESCRIPTION

A detailed description of one or more embodiments of the disclosed apparatus and method are presented herein by way of exemplification and not limitation with reference to the Figures.

Figure 1:
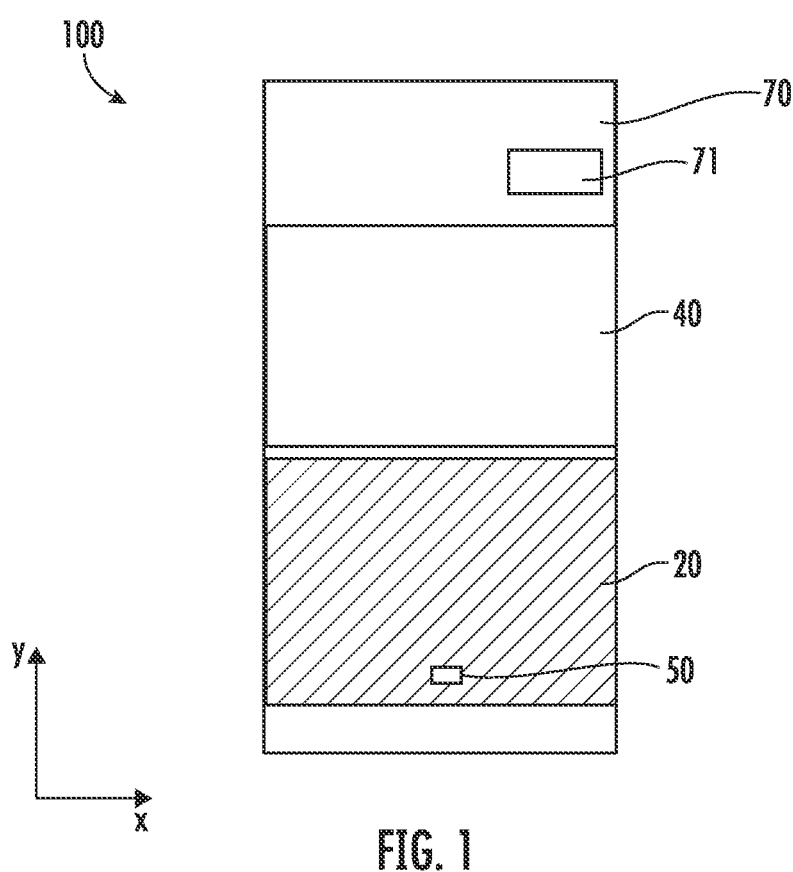
FIG. 1 is a schematic illustration of a front view of a heating, ventilation, air conditioning, or refrigeration (HVAC/R) device having a gas detector.

FIG. 1 is a schematic illustration of a front view of a vertically arranged heating, ventilation, air conditioning, or refrigeration (HVAC/R) device 100 having an indoor heat exchanger section 20, a fan section 40, a gas sensing module 50, and a control unit 70. The vertically arranged HVAC/R device 100 can be configured as an indoor unit for a residential HVAC system (e.g., air conditioner, heat pump, and the like). Although depicted vertically in FIG. 1, a horizontally arranged HVAC/R device 100, such as for installation in an attic space, are within the scope of this disclosure.

Figure 2:
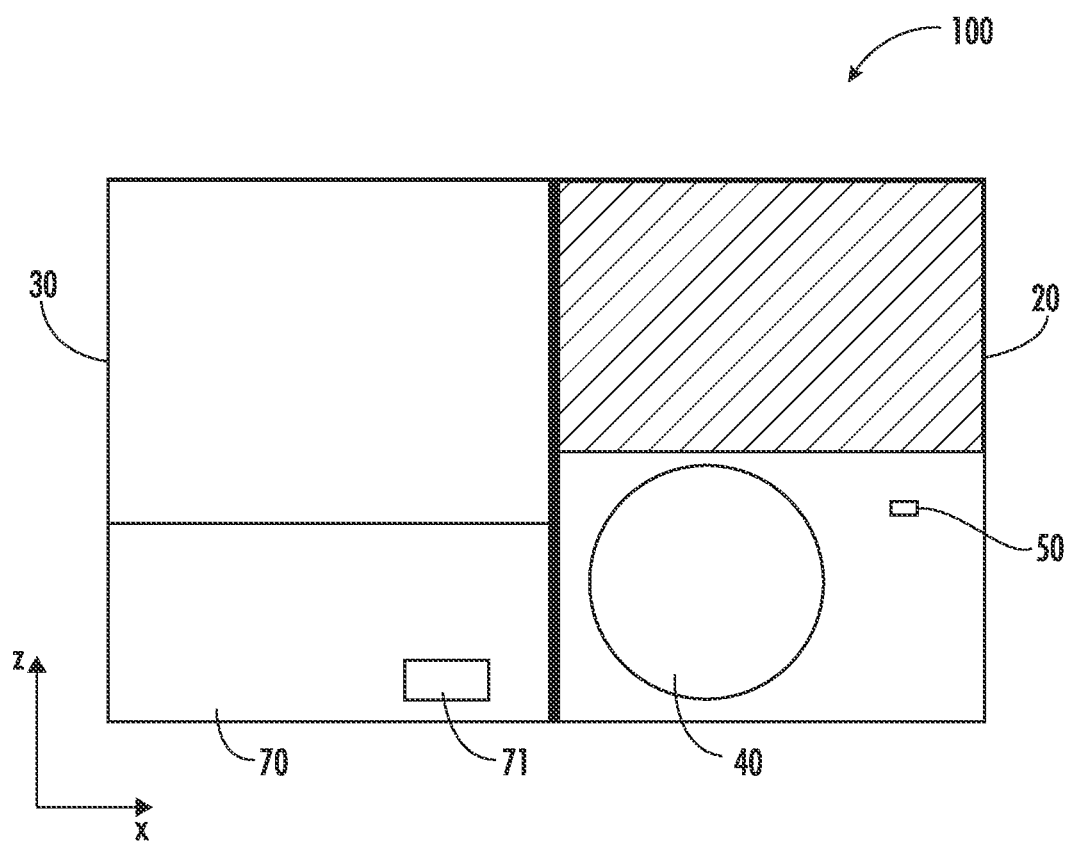
FIG. 2 is a schematic illustration of a top view of a heating, ventilation, air conditioning, or refrigeration (HVAC/R) device having a gas detector.

FIG. 2 is a schematic illustration of a top view of a horizontally arranged HVAC/R device 100 having an indoor heat exchanger section 20, an outdoor heat exchanger section 30, a fan section 40, a gas sensing module 50, and a control unit 70. A divider can separate the indoor and the outdoor heat exchanger sections. The horizontally arranged HVAC/R device can be configured as a commercial HVAC device (e.g., such as a rooftop air conditioner, heat pump, and the like).

Figure 3:
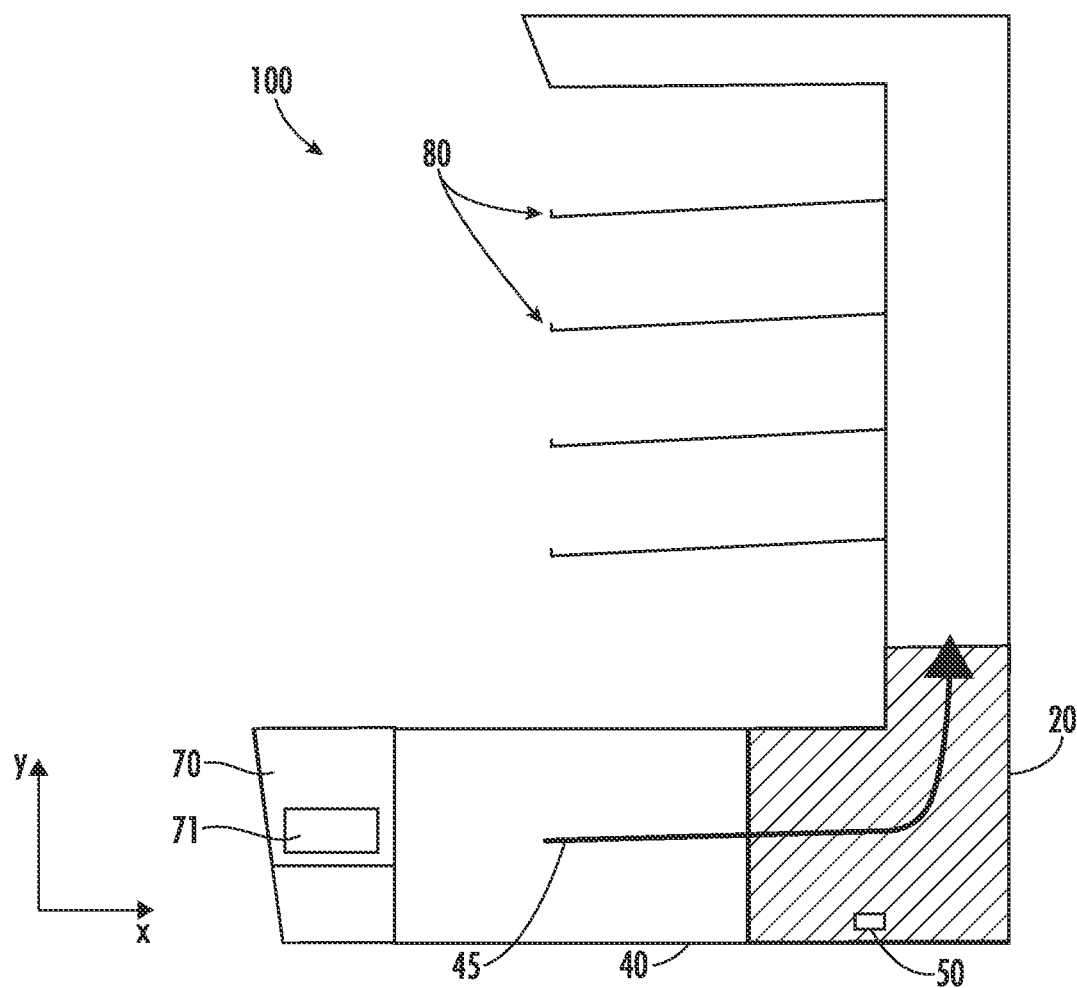
FIG. 3 is a schematic illustration of a side view of a heating, ventilation, air conditioning, or refrigeration (HVAC/R) device having a gas detector.

FIG. 3 is a schematic illustration of a side view of a HVAC/R device 100 having an indoor heat exchanger section 20 (e.g., evaporator section), a fan section 40, a gas sensing module 50, a control unit 70, and product shelves 80. The HVAC/R device 100 can be configured as a refrigerated display case (e.g., for refrigerating self-service retail products). The order of the indoor heat exchanger section 20 and the fan section 40 along an air flow pathway 45 can be reversed.

The indoor heat exchanger section 20 can include a heat exchanger of any suitable heat exchanger technology, configuration, orientation, or design. For example, the indoor heat exchanger section 20 can include a finned tube heat exchanger (e.g., round tube plate fin (RTPF), spike fin, and the like), or a flat tube heat exchanger (e.g., microchannel heat exchanger), or the like. A heat exchanger of the indoor heat exchanger section 20 can be configured in any suitable shape and orientation, such as a flat configuration, a flat inclined configuration, a folded and/or bent configuration (e.g., such as having a C, J, L, M, N, U, V, W, or Z shaped configuration, or the like), or the like. The heat exchanger of the indoor heat exchanger section 20 can be configured for single-pass or multi-pass configuration (e.g., where refrigerant contained within the heat exchanger crosses through, and is in thermal communication with, an air stream external the heat exchanger more than one time per loop through a vapor compression cycle).

The fan section 40 can include any suitable fan technology, including axial flow, centrifugal flow, and mixed flow fans, to move air through the HVAC/R device 100. The fan section 40 can further include flow guides, louvers, and the like for directing flow into, through, and/or from the fan section 40. Although the fan section 40 can be located downstream of the indoor heat exchanger section 20 as in FIG. 1, as noted above the opposite configuration where the indoor heat exchanger section 20 is located above the fan section 40 can also be used.

Figure 4:
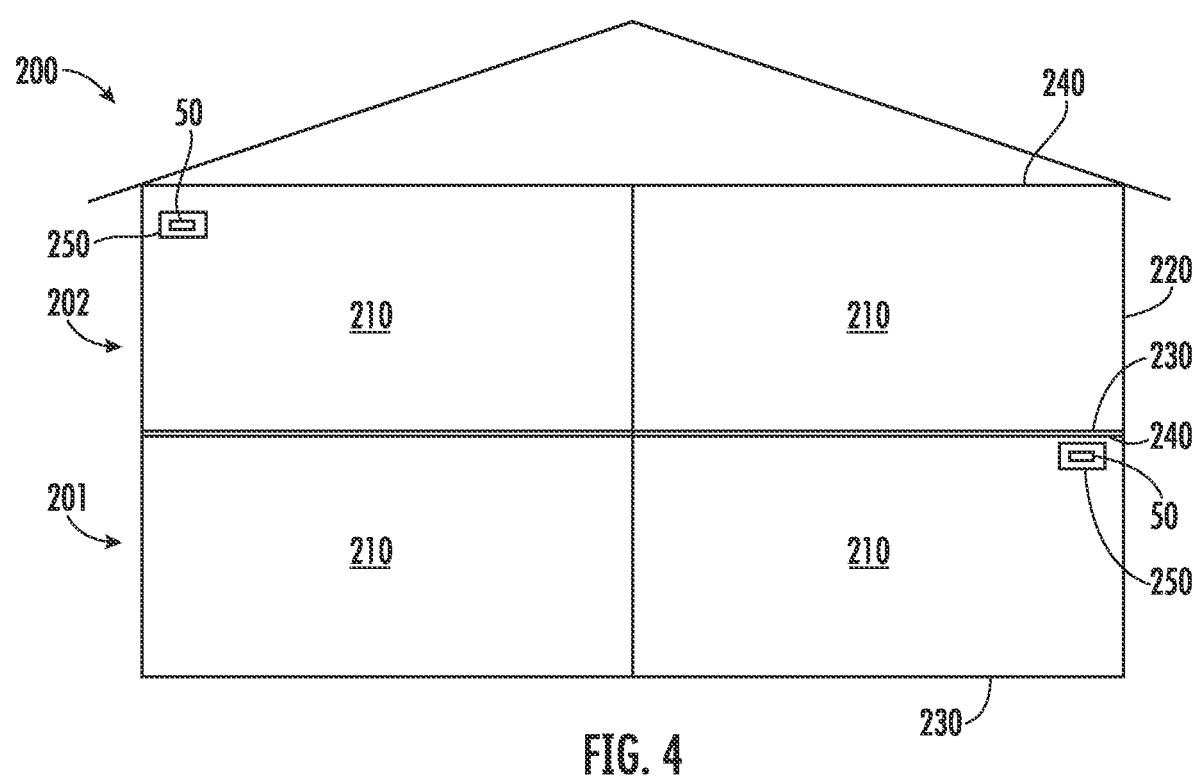
FIG. 4 is a schematic illustration of a building having a gas detector.

FIG. 4 is a schematic illustration of a side view of a building 200 having levels 201, 202, walls 220, floors 230, and ceilings 240. The building 200 can include one or more hazard detection devices 250. For example, the hazard detection device 250 can include a sensor of a gas phase hazard such as a smoke detector, a carbon monoxide (CO) detector, a flammable gas detector, radon detector, oxygen sensor, carbon dioxide ($CO_2$) monitor, pollutant gas detector (e.g., volatile organic compound (VOC) gas detector, particulate matter (PM) detector (e.g., PM 10, PM 5, or PM 2.5 corresponding to detectors capable of detecting particles having average particle diameters of less than or equal to about 10 micrometers (μm), 5 μm, and 2.5 μm respectively), formaldehyde ($CH_2O$) detector, lead (Pb) detector, pesticide detector, nitrogen dioxide ($NO_2$) detector, or the like), or the like. The hazard detection device 250 can include a gas sensing module 50, such as described herein.

Figure 5:
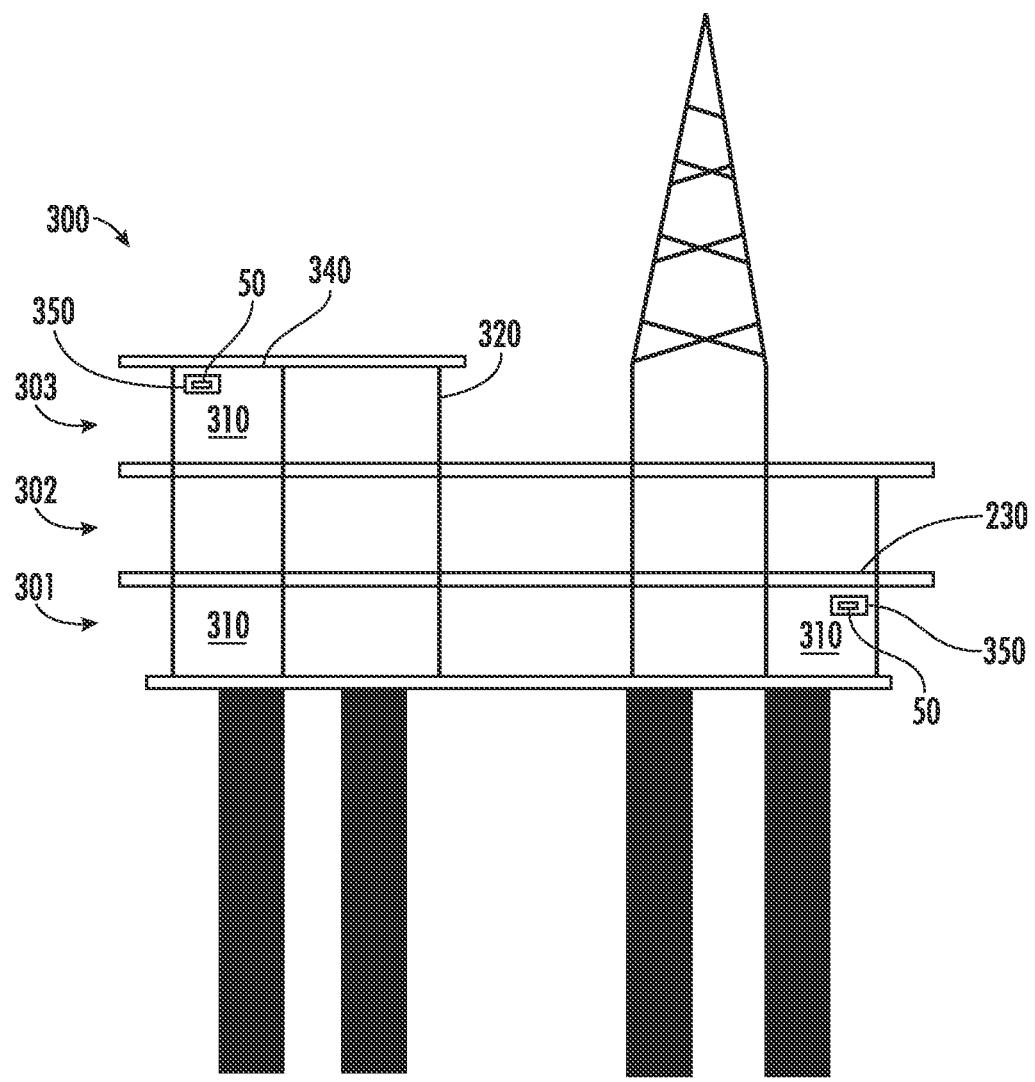
FIG. 5 is a schematic illustration of an oil rig having a gas detector.

FIG. 5 is a schematic illustration of a side view of an oil rig 300 having levels 301, 302, 303, walls 320, floors 330, and ceilings 340. The oil rig 300 can include one or more hazard detection devices 350 for monitoring for the presence of hazards to workers on the oil rig 300. For example, the hazard detection device 350 can include a sensor of a gas phase hazard such as a petroleum gases, hydrogen sulfide ($H_2S$), engine exhaust (e.g., diesel exhaust), natural gas or constituents thereof, including other flammable or combustible gases (e.g., butane, butene, propane, propene, methane, ethane, ethene, or mixtures thereof). The hazard detection device 350 can include a gas sensing module 50, such as described herein.

Figure 6:
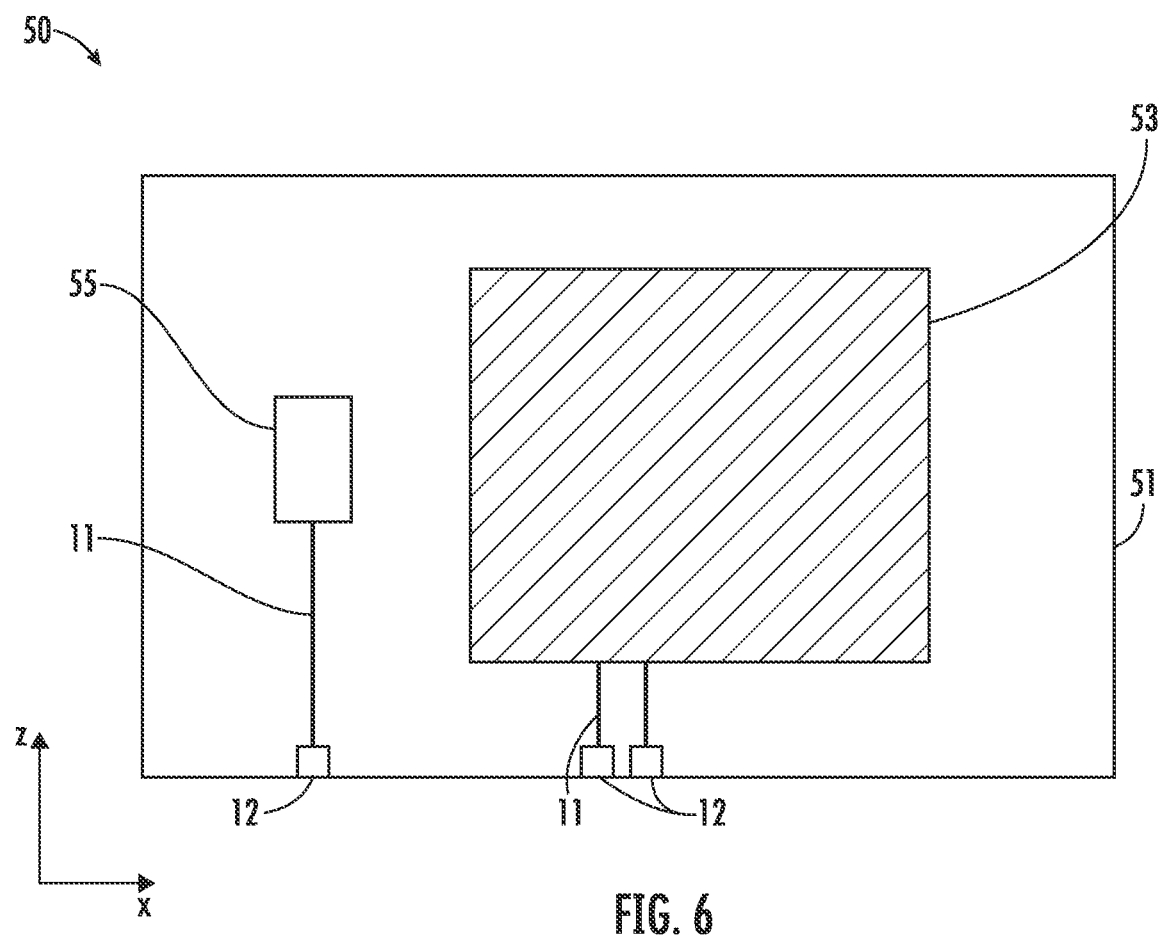
FIG. 6 is a schematic illustration of a gas sensing module.

The gas sensing module 50 can include a gas sensing core 53 and a condition sensor 55 (e.g. an environmental condition sensor such as a temperature, humidity, pressure sensor, a combination including at least one of the foregoing, or the like). The gas sensing core 53 and/or the condition sensor 55 can be mounted on a circuit board 51. For example, as in FIG. 6, electrically conductive traces 11 of the circuit board 51 can act to electrically link the electrical outputs of the gas sensing core 53 and the condition sensor 55 to one or more output terminals 12 of the gas sensing module 50. As used herein, output terminals can refer to any means of providing an electrically conductive interface to the electrical output signal of the referenced element, e.g., including terminal blocks, pins, blades, conductors, conductive traces, and the like. Optionally, the condition sensor 55 can be mounted in direct contact with a surface of the gas sensing core 53 or can be an internal sensor configured to sense a condition internal to the gas sensing core 53 (e.g., configure to measure internal core temperature, humidity, or the like). For example, the condition sensor 55 can be mounted on top of the gas sensor core 53. In another example, the condition sensor 55 can be mounted on the circuit board 51 directly contacting a side of the gas sensing core 53.

The gas sensing core 53 can include any suitable technology of gas phase monitoring. For example, the gas sensing core 53 can rely on nondispersive infrared (NDIR), ultrasonic, or electrochemical measurement technology. The methods disclosed herein can improve the accuracy of the gas sensing module 50 by dismissing erroneous alarms whose conditions mimic that of water condensation on the gas sensing core 53.

The control unit 70 can include a controller 71, such as a field programmable gate array (FPGA), central processing unit (CPU), application specific integrated circuits (ASIC), or the like. The control unit 70 can be disposed remote of the gas sensor 50. Electrical conductors can extend between the controller 71 and the gas sensing module 50 for interfacing one or more output terminals of the gas sensing module 50 to one or more input terminals of the controller 71. Alternatively, the controller 71 can include a wireless receiver and one or more outputs of the gas sensing module 50 can be wirelessly transmit to the controller 71 (e.g., via a wireless transmitter, such as a Bluetooth transmitter, low energy Bluetooth (BLE) transmitter, NFC transmitter, or the like) using a transmitter disposed in electrical communication with the gas sensing module 50.

A problem with the systems, such as described above, is that they can erroneously indicate the presence of a target gas when condensation occurs on the gas sensing core 53. Condensation on the gas sensing core 53 can be particularly pronounced in HVAC/R devices 100 due to the relatively cold surface temperatures of some of the components during operation (e.g., evaporator and connected piping and equipment). A method of overcoming condensation induced false positive indications from the gas sensing core 53 can include providing a heater for heating areas of the gas sensor module 50 susceptible to condensation (e.g., the gas sensing core 53 and adjacent areas). However, such methods can be electrically inefficient, place additional limitation on system design, e.g. power storage, distribution, and control associated with one or more heaters, and/or raise other concerns, e.g., such as safety concerns associated with co-locating an electric heater with a sensor used to detect combustible gases. Accordingly, the disclosed method can dismiss false positive indications from the gas sensing core 53 in a safe and robust way by analyzing changes in the output signals of gas sensing core 53 and condition sensor 55 over time.

Figure 7:
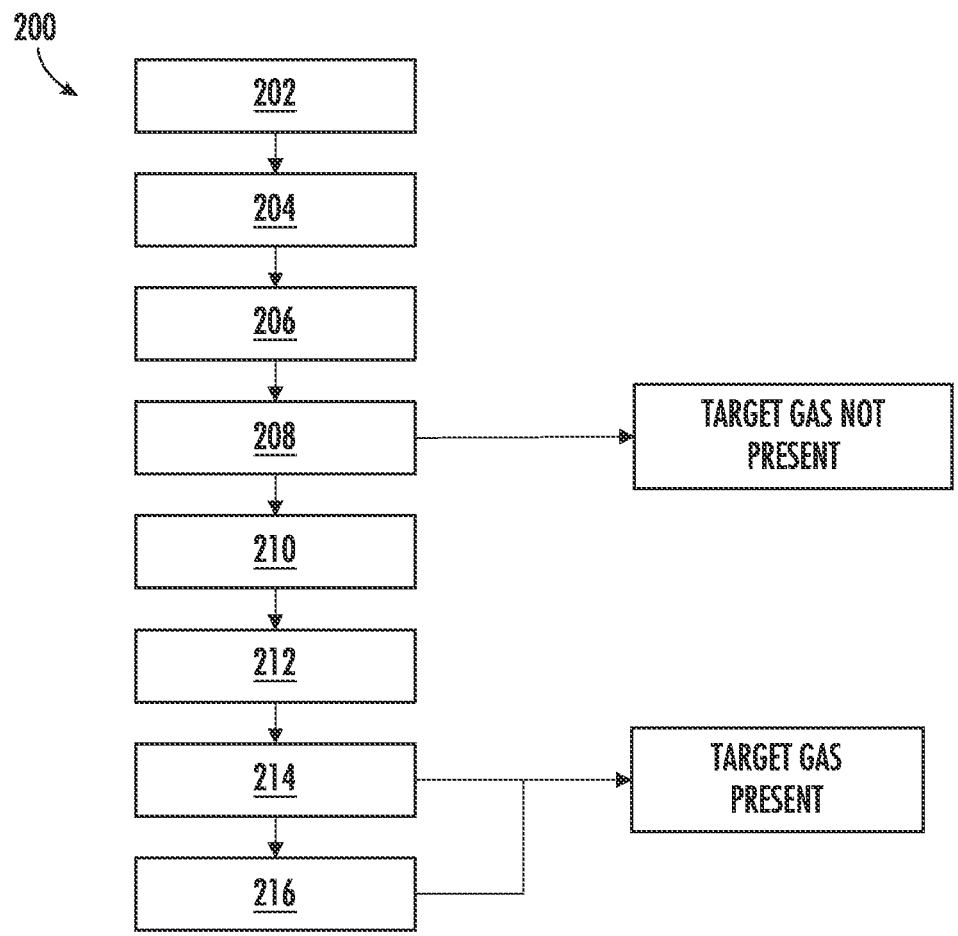
FIG. 7 is a schematic illustration of a method of sensing a target gas.

FIG. 7 is a schematic illustration of a method 200 of sensing the presence of a target gas in a gas volume. A first step 202 of method 200 can include providing a gas sensor module 50, having a gas sensing core 53 configured for sensing a target gas and a condition sensor 55, within the gas volume. The gas volume can be a volume within a housing of the HVAC/R device 100, e.g., a volume adjacent and/or encompassing refrigerant bearing components of the HVAC/R device 100. For example, the gas volume can include at least a portion of the indoor heat exchanger section 20. The gas volume can encompass an evaporator of the HVAC/R device 100. The gas volume can extend under an evaporator along a floor of the HVAC/R device 100. Locating the gas sensor module 50 near to the floor of the HVAC/R device 100 can speed detection of the refrigerant gases because the refrigerant can be denser than air and can tend to drop towards and accumulate near the floor first during a leakage scenario. The gas volume can be disposed within a room 210, 310 or other area of a building 200, oil rig 300, or other site where occupants or proximate workers may be exposed to hazardous gases (e.g., radon, hydrogen sulfide, and the like).

A second step 204 of method 200 can include providing the controller 71 configured in electrical communication with the gas sensing core 53 and the condition sensor 55. The controller 71 can read the parameter output from the condition sensor 55 and target gas measurement output from the gas sensing core 53 to decide whether an indication of positive gas detection by the gas sensing core 53 is representative of actual gas detection, or of a false positive. For example, the controller 71 can compare changes in data output from condition sensor 55 with stored information (e.g., stored in memory of the control unit 70, such as random access memory (RAM), non-volatile memory, semi-volatile memory, or the like) describing how the condition sensor 55 parameter output changes during condensation conditions. If the target gas detection by the gas sensing core 53 is a true positive gas detection, then the controller 71 can initiate a notification, mitigation, and/or abatement process. For example, issuing an alarm, commencing a ventilation process, transitioning to a refrigerant conservation mode (e.g., including steps to isolate refrigerant in portions of the system), or other mitigation processes.

As used herein flammable refrigerant can refer to any refrigerant that is, or can be, classified under the A2L or A3 classification within the guidelines set forth by the American Society of Heating, Refrigerating and Air Conditioning Engineers (ASHRAE) Standard 34 Safety Classification in force as of the filing of the present application. For example, flammable refrigerants can include R-1234yf (2,3,3,3-tetrafluoropropene), R-1270 (propene), R-143a (1,1,1-trifluoroethan), R-152a (1,1-difluoroethane), R-23 (trifluoromethane), R-32 (difluoromethane), R-170 (ethane), R-290 (propane), and the like, and combinations comprising one or more of the foregoing, including blends thereof, such as for further example R-411A or R-411B (each a blend of R-1270, R-22 (chlorodifluoromethane), and R-152a), R-415A or R-415B (each a blend of R-22 and R-152a), or R-454A, R454B, or R-454C (each a blend of R-32 and R-1234yf (2,3,3,3-tetrafluoropropene)), and the like.

A third step 206, of method 200 can include allowing at least a portion of fluid within the gas volume to fluidly interact with the gas sensing core 53. For example, fluid in the gas volume can be pushed, or pulled, past the gas sensing core 53 by a fan within the fan section 40. In another example, the gas sensing core 53 can be strategically positioned near likely target gas locations (e.g., such as ceilings for smoke detectors, end turns of an evaporator coils for refrigerant gas detectors, and the like). Such placement can allow the gas sensing core 53 to fluidly interact with a portion of fluid within the gas volume more likely to contain target gases of the gas sensing core 53.

A fourth step 208 of the method 200 can include monitoring with the controller 71 a target gas measurement output from the gas sensing core 53 (e.g., an electrical output signal). The target gas measurement output can be any suitable electrical output signal that can communicate a change in conditions at the core (e.g., a change in target gas concentration). For example the target gas measurement output from the gas sensing core 53 can be discrete (e.g., digital, on/off, true/false, and the like) or continuous (e.g., analog, having a signal strength, or output value, corresponding to concentration of gases interacting with the gas sensing core 53). The fourth step 208 can further include not annunciating, signaling, or indicating the presence of a target gas when the gas sensing core 53 output value is below a target gas measurement threshold value. The method 200 can include transitioning from the fourth step 208 to a fifth step 210 when the gas sensing core 53 output value exceeds a target gas measurement threshold value.

The target gas measurement threshold value can be configured based on the type of gas being monitored and the application of the gas sensor. In an HVAC/R application the target gas threshold value can be a function of the type of refrigerant used in the HVAC/R device 100, the type of target gas sensing technology deployed, and/or the type of electrical output signal supplied by the gas sensing core 53. For example, the gas sensing core 53 can be configured as a combustible gas sensor where the target gas measurement threshold value can be set based on the combustibility of the target gas in air. Such target gas measurement threshold value can be equal to from about 5% to about 25% of the lower flammability limit (LFL) concentration of the target gas. For example, the target gas measurement threshold value can be set to about 16.6% of the LFL of R-454B (e.g. a blend of 68.9 weight % R-32 and 31.1 weight % R-1234yf). In another example, in an HVAC/R device 100 having a gas sensing core 53 with a discrete electrical output signal, the target gas measurement threshold value can be set to 1 (e.g., "on", or "true", or the like).

The fifth step 210 of the method 200 can include monitoring with the controller 71 a parameter output from the condition sensor 55. In addition to electrically interfacing with the electrical output of the gas sensing core 53, the controller 71 can be configured in electrical communication with the condition sensor 55 and can simultaneously, or nearly simultaneously, monitor its electrical output signal.

A sixth step 212 of the method 200 can include recording a minimum parameter output value from the condition sensor 55 to a data storage device in electrical communication with the controller 71 (e.g., storing in volatile memory such as random access memory (RAM), non-volatile memory, semi-volatile memory, or the like). Recording the minimum parameter output value from the condition sensor 55 can include setting a timespan (e.g., timeframe and/or number of prior signals from the condition sensor 55) over which the minimum parameter output is determined. That timespan can be chosen based on the dynamics of the condensation phenomena that occur on the gas sensing core 53. For example, the timespan can be set to 5 minutes of prior readings from the temperature sensor 55, or 4 minutes, or 3 minutes, or 2 minutes, or 90 seconds, or 75 seconds, or 60 seconds, or 45 seconds, or 30 seconds, or 15 seconds, or 10 seconds, or 5 seconds of prior readings from the condition sensor 55. The sixth step 212 can include recording a timestamp (e.g., representative of actual time) to the data storage device for each cycle that the controller 71 collects data.

The timespan over which the minimum parameter output is established can depend on the data collection cycle time (e.g., related to refresh rate) of the controller 71 rather than on a set time interval. The sixth step 212 can include recording the target gas measurement output signal from the gas sensing core 53 throughout the timespan. For example, the minimum parameter output from the condition sensor 55 can be decided based on a static or dynamic number of previously collected data points, e.g., the minimum value of the past 200 or less data points, e.g., the past 200, 150, 100, 75, 50, 30, 20, 10, or 5 data points, or the like. The data refresh rate of the controller 71 can be less than or equal to about 10 Hertz (Hz), e.g., less than or equal to about 5 Hz, or about 4 Hz, or about 3 Hz, or about 2 Hz, or about 1 Hz, or about 0.5 Hz, or about 0.33 Hz, or about 0.25 Hz or about 0.2 Hz, or the like. The controller 71 can be configured to update the minimum parameter output value stored in the data storage device with every data collection cycle of the controller 71. For example, the minimum parameter output of condition sensor 55 stored in the memory can be updated at the same data refresh rate as the controller 71.

A seventh step 214 of the method 200 can include calculating (e.g., with the controller 71) a parameter difference between the stored minimum parameter output value and the instant parameter output from the condition sensor 55. Further, the seventh step 214 can include comparing the calculated parameter difference to a parameter difference threshold value. The parameter difference threshold value can be configured based on empirical results showing that condensation has occurred on the gas sensing core 53. For example, the condition sensor 55 can be configured as a temperature sensor where the parameter output is a temperature measured by the condition sensor 55 and the parameter difference threshold value is a temperature difference threshold set to less than or equal to about 5° C., e.g., about 4° C., or about 3° C., or about 2.5° C., or about 2.4° C., or about 2.35° C., or about 2.3° C., or about 2.25° C., or about 2.2° C., or about 2.15° C., or about 2.1° C., or about 2.05° C., or about 2.0° C. In another example, the condition sensor 55 can be configured as a humidity sensor where the parameter output is a humidity value (e.g., relative humidity) measured by the condition sensor 55 and the parameter difference threshold value is a humidity difference threshold set to less than or equal to about 25%, e.g., about 20%, or about 18%, or about 16%, or about 15%, or about 14%, or about 13%, or about 12%, or about 11%, or about 10%, or about 9%, or about 8%, or about 7%, or about 6%, or about 5%.

Still further, the seventh step 214 can include indicating the presence of a target gas when a parameter difference is less than or equal to the parameter difference threshold value and the target gas measurement output from the gas sensing core 53 exceeds the target gas measurement threshold value. The method 200 can include advancing from the seventh step 214 to an eighth step 216 when the calculated parameter difference exceeds the parameter difference threshold value.

The eighth step 216 of the method 200 can include calculating (e.g., with the controller 71) a rate of change of the parameter output of the condition sensor 55 with respect to time. For example, the rate of change of the parameter output of the condition sensor 55 can be calculated based on the difference between the instant parameter output value (e.g., the value from last data collection cycle of the controller 71) and the recorded minimum parameter output value (e.g., such as the minimum value stored in memory in the sixth step 212). In another example, the rate of change of the condition sensor 55 parameter output can be calculated based on the difference between one or more parameter output values (e.g., instant values and/values stored in memory of the data storage device) divided by the temporal difference of the recordings (e.g., as determined from the time elapsed between timestamps of the recordings). The eighth step 216 can include indicating the presence of the target gas when the calculated rate of change of the parameter with respect to time is less than or equal to a rate threshold value, the parameter difference exceeds the parameter difference threshold, and the target gas measurement output from the gas sensing core 53 exceeds the target gas measurement threshold value. The eighth step 216 can include not indicating the presence of a combustible gas mixture, and/or indicating a false positive, when the calculated rate of change of the parameter with respect to time exceeds the rate threshold value, the parameter difference exceeds the parameter difference threshold, and the target gas measurement output from the gas sensing core 53 exceeds the target gas measurement threshold value.

The rate threshold value can be configured based on empirical results showing that condensation has occurred on the gas sensing core 53. For example, the condition sensor 55 can be configured as a temperature sensor where the parameter output is a temperature measured by the condition sensor 55, the calculated rate of the parameter with respect to time is a rate of temperature change, and the rate threshold value can be set to about 1.5° C./minute, e.g., about 1.55° C./minute, or about 1.6° C./minute, or about 1.65° C./minute, or about 1.67° C./minute, or about 1.69° C./minute, or about 1.71° C./minute, or about 1.72° C./minute, or about 1.73° C./minute, or about 1.74° C./minute, or about 1.75° C./minute, or about 1.76° C./minute, or about 1.77° C./minute, or about 1.78° C./minute, or about 1.79° C./minute, or about 1.8° C./minute, or about 1.85° C./minute, or about 1.9° C./minute, or about 2.0° C./minute.

In another example, the condition sensor 55 can be configured as a humidity sensor where the parameter output is a humidity value (e.g., relative humidity) measured by the condition sensor 55, the calculated rate of change of the parameter with respect to time is a rate of percent humidity change, and the rate threshold value can be set to about 25%/second, e.g., about 20%/second, or about 18%/second, or about 16%/second, or about 15%/second, or about 14%/second, or about 13%/second, or about 12%/second, or about 11%/second, or about 10%/second, or about 9%/second, or about 8%/second, or about 7%/second, or about 6%/second, or about 5%/second, or about 4%/second, or about 3%/second, or about 2%/second.

Although laid out in numerical order, any two or more steps of the method 200 can be performed sequentially or simultaneously. For example, monitoring the target gas measurement output from the gas sensing core 53 as in step four 208, monitoring the parameter output of the condition sensor 55 as in the fifth step 210, recording a minimum parameter output value from the condition sensor 55 to a data storage device as in the sixth step 212, calculating a parameter difference between the stored minimum parameter output value and the instant parameter output from the condition sensor 55 as in the seventh step 214, and calculating a rate of change of the parameter output of the condition sensor 55 with respect to time as in the eighth step 216, can be performed simultaneously with all other steps of the method 200.

The term "about" is intended to include the degree of error associated with measurement of the particular quantity based upon the equipment available at the time of filing the application.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

While the present disclosure has been described with reference to an exemplary embodiment or embodiments, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the essential scope thereof. Therefore, it is intended that the present disclosure not be limited to the particular embodiment disclosed as the best mode contemplated for carrying out this present disclosure, but that the present disclosure will include all embodiments falling within the scope of the claims.

What is claimed is:

1. A method of indicating the presence of a target gas in a gas volume comprising:
providing a gas sensing core, configured for detection of the target gas, and a condition sensor within the gas volume,
providing a controller disposed in electrical communication with the gas sensing core and the condition sensor,
allowing gas within the gas volume to fluidly interact with the gas sensing core,
monitoring with the controller a target gas measurement output from the gas sensing core,
monitoring with the controller a parameter output from the condition sensor,
recording a parameter output minimum value in a memory of the controller, calculating with the controller a parameter difference, wherein the parameter difference is the difference between the minimum value of the parameter and an instant value of the parameter, calculating with the controller a rate of change of the parameter with respect to time, and indicating the presence of a target gas is detected in the gas volume when the target gas measurement exceeds a target gas measurement threshold value and the parameter difference is less than a parameter difference threshold value.

2. The method of claim 1, further comprising indicating the presence of a target gas is detected in the gas volume when the target gas measurement exceeds the target gas measurement threshold value, the parameter difference exceeds the parameter difference threshold value, and the rate of change of the parameter with respect to time is less than a rate threshold value.

3. The method of claim 2, further comprising not indicating the presence of the target gas is detected in the gas volume when target gas measurement exceeds a target gas threshold value, the parameter difference exceeds the parameter difference threshold value, and the rate of change of the parameter with respect to time exceeds a rate threshold value.

4. The method of claim 1, further comprising locating the gas sensing core and the condition sensor in an HVAC/R device, wherein the gas volume is adjacent a flammable refrigerant containing component of the HVAC/R device.

5. The method of claim 1, wherein indicating a presence of the target gas comprises signaling to a system controller of a HVAC/R device that target gas is detected, activating an indicator light in electrical communication with the controller, annunciating an alarm through a speaker in electrical communication with the controller, or a combination comprising at least one of the foregoing.

6. The method of claim 1, wherein the recording the parameter output minimum value further comprises recording the parameter output minimum value from the condition sensor over a timespan.

7. The method of claim 1, wherein the calculating with the controller a rate of change of the parameter output with respect to time further comprises calculating the rate of change from the parameter output minimum value and a corresponding timestamp, to the instant parameter output and corresponding instant timestamp.

8. The method of claim 1, wherein the condition sensor comprises a temperature sensor, or a humidity sensor.

9. The method of claim 1, wherein the gas sensing core comprises a combustible gas sensor, a flammable gas sensor, a radon sensor, a smoke sensor, a carbon monoxide sensor, a hydrogen sulfide sensor, a particulate matter sensor, a volatile organic compound sensor, an oxygen sensor, a formaldehyde sensor, a lead sensor, a pesticide sensor, a nitrogen dioxide sensor, or a carbon dioxide sensor.

10. The method of claim 1, wherein the target gas measurement threshold value is greater than or equal to 5% and less than or equal to 25% of the lower flammability limit of a flammable refrigerant contained within a flammable refrigerant containing component of a HVAC/R device.

11. The method of claim 1, wherein the condition sensor comprises a temperature sensor, and wherein the parameter difference threshold value is greater than 2° C.

12. The method of claim 1, wherein the condition sensor comprises a humidity sensor, and wherein the parameter difference threshold value is greater than 5% relative humidity.

13. The method of claim 1, wherein the condition sensor comprises a temperature sensor, and wherein the rate threshold value is greater than 1.5° C./minute.

14. An HVAC/R system comprising:

a vapor compression device containing flammable refrigerant and a system controller, a gas sensing module disposed in fluid communication with a gas volume surrounding at least a portion of the vapor compression device, wherein the gas sensing module comprises a gas sensing core configured to measure a target gas measurement output and a condition sensor configured to measure a parameter output, a controller disposed in electrical communication with the system controller, the gas sensing core and the condition sensor, wherein the controller is configured to;

monitor a target gas measurement output from the gas sensing core;

monitor a parameter output from the condition sensor;

record a parameter output minimum value in the memory;

calculate a parameter difference, wherein the parameter difference is the difference between the minimum value of the parameter and an instant value of the parameter;

calculate a rate of change of the parameter with respect to time;

determine that a target gas is detected in the gas volume when the target gas measurement exceeds a target gas measurement threshold value, and the parameter difference is less than a parameter difference threshold value; and initiate a control action in response to a determination that a target gas is detected by the gas sensing module.

15. An HVAC/R system comprising:

a vapor compression device containing flammable refrigerant and a system controller, a gas sensing module disposed in fluid communication with a gas volume surrounding at least a portion of the vapor compression device, wherein the gas sensing module comprises a gas sensing core configured to measure a target gas measurement output and a condition sensor configured to measure a parameter output, a controller disposed in electrical communication with the system controller, the gas sensing core, and the condition sensor, wherein the controller is configured to initiate a control action in response to a determination that a target gas is detected by the gas sensing module, wherein the determination of the gas sensing core is disregarded as erroneous when:

the target gas measurement exceeds a target gas measurement threshold value, a parameter difference exceeds a parameter difference threshold value, wherein the parameter difference comprises a difference between the parameter output and a minimum parameter output value stored in a memory of the controller, and a rate of change of the parameter with respect to time exceeds a rate threshold value, wherein the rate of change of the parameter with respect to time comprises the parameter difference divided by a timespan between the instant time and a timestamp of the minimum parameter output value was stored in the memory of the controller.

* * * * *